United States Patent [19]

Chang et al.

[11] Patent Number: 4,961,429
[45] Date of Patent: Oct. 9, 1990

[54] DIASTOLIC PRESSURE SENSOR

[76] Inventors: Kuo Wei Chang; Shine Chang, both of 32 Buckman Dr., Lexington, Mass. 02173

[21] Appl. No.: 462,803

[22] Filed: Feb. 2, 1983

[51] Int. Cl.$^5$ ............................................. A61B 5/021
[52] U.S. Cl. ...................................... 128/680; 128/708
[58] Field of Search ................ 128/672, 677, 680–683, 128/687, 708

[56] References Cited

U.S. PATENT DOCUMENTS

| | | | |
|---|---|---|---|
| 2,827,040 | 3/1958 | Gilford | 128/683 X |
| 3,878,834 | 4/1975 | Sanderson | 128/680 |
| 4,188,955 | 2/1980 | Sakamoto et al. | 128/680 |
| 4,214,589 | 7/1980 | Sakamoto et al. | 128/680 |
| 4,216,779 | 8/1980 | Squires et al. | 128/708 X |
| 4,262,674 | 4/1981 | Uemura et al. | 128/680 |
| 4,271,843 | 6/1981 | Flynn | 128/681 |
| 4,328,810 | 5/1982 | Hill et al. | 128/680 |
| 4,356,827 | 11/1982 | Uemura et al. | 128/680 |
| 4,408,614 | 10/1983 | Weaver et al. | 128/680 |
| 4,459,991 | 7/1984 | Hatschek | 128/681 |
| 4,592,365 | 6/1986 | Georgi | 128/682 X |

FOREIGN PATENT DOCUMENTS 0869032  4/1971  Canada ............................... 128/680

*Primary Examiner*—Angela D. Sykes
*Attorney, Agent, or Firm*—Samuels, Gauthier & Stevens

[57] ABSTRACT

An arterial pressure pulse is sensed and the next succeeding Korotkoff sound is sensed and the time lag between the two is measured. When the time lag between the two cannot be measured, the cuff pressure can be taken as a true measure of diastolic pressure.

6 Claims, 2 Drawing Sheets

DIASTOLIC PRESSURE SENSOR

BACKGROUND AND BRIEF SUMMARY OF THE INVENTION

This invention relates to blood pressure measurement involving low frequency vibration detection and phase discrimination. The invention is particularly applicable to blood pressure measurement of chemical warfare garbed casualties. The need to obtain vital signs information in any casualty is indisputable. The following vital signs are typically measured, systolic pressure, mean arterial pressure, diastolic pressure, pulse rate, exhalation rate, and tidal volume exhaled. The present invention is directed to a method of measuring diastolic pressure.

Although the diastolic pressure is a uniquely defined parameter, there is uncertainty with regard to its determination when a sphygmomanometer is used. Over the past 30 years, Phase V, the cessation of sound and Phase IV, the beginning of muffling, had been used as criteria for determination of diastolic pressure. The true diastolic pressure, as measured with an indwelling transducer, is generally believed to be between the fourth and the fifth phase. The current recommendation of the American Heart Association is to record both Phase IV and V readings. For certain groups of people, including infants, patients with aortic regurgitation, and normal subjects during or following exercise, the muffling of sound is not always easy to discern, and the Korotkoff sounds can be heard all the way to low or even zero cuff pressure. In such subjects, the error in diastolic pressure determination can be quite large.

The diminution of time lag between the arrival of each arterial pressure pulse and the initiation of Korotkoff sound has been found to be a more reliable and accurate criterium for diastolic pressure indexing or measurement.

The present invention broadly measures the time lag between arterial pressure pulse and the next subsequent Korotkoff sound. When the time lag between the pressure pulse and the sound is essentially zero the pressure pulse may be read as the true diastolic pressure.

The method of our invention broadly comprises detecting a first signal corresponding to an arterial pressure pulse; sensing a second subsequent signal corresponding to a Korotkoff sound, determining the time lag between the signals; and providing an output corresponding to diastolic pressure when there is no measurable time lag between the signals.

DESCRIPTION OF THE PREFERRED EMBODIMENT(S)

The arrival of an arterial pressure pulse can be determined from the air pressure oscillation within a cuff bladder for example a cuff bladder for blood pressure measurement such as available from PyMaH Corp., which cuff bladder is the basis of the following description. These are pressure oscillations called "oscillometric" signals and are generated by the striking action of the arterial pressure wave train against the proximal edge of the occluding cuff. The oscillometric signal is present at cuff pressure both considerably above the systolic pressure and below the diastolic pressue.

In the cuff is mounted a piezo-electric sensor or electret transducer. The mounted signal detected by the piezo-electric sensor or electret transducer (with low frequency cut off) placed over an artery at the distal third portion of the cuff has essentially two parts; a low frequency component (roughly below 20 Hz) associated with direct physical pushing of the sensor diaphragm by the arterial pressure wave, and a characteristic frequency component (between 20 and 200 Hz, approximately) associated with arterial wall motion and turbulent blood flow. This characteristic frequency component is responsible for the production of Korotkoff sounds.

With a supra-systolic cuff pressure, there is no Korotkoff sound and the sensor signal contains only the low frequency component which appears with each heart beat. Because blood flow is prevented, the sensor signal is generated by the indirect push against the backside of the sensor by the bladder. The bladder can "feel" the arterial pressure wave train through coupling at the proximal end.

Figure 1:
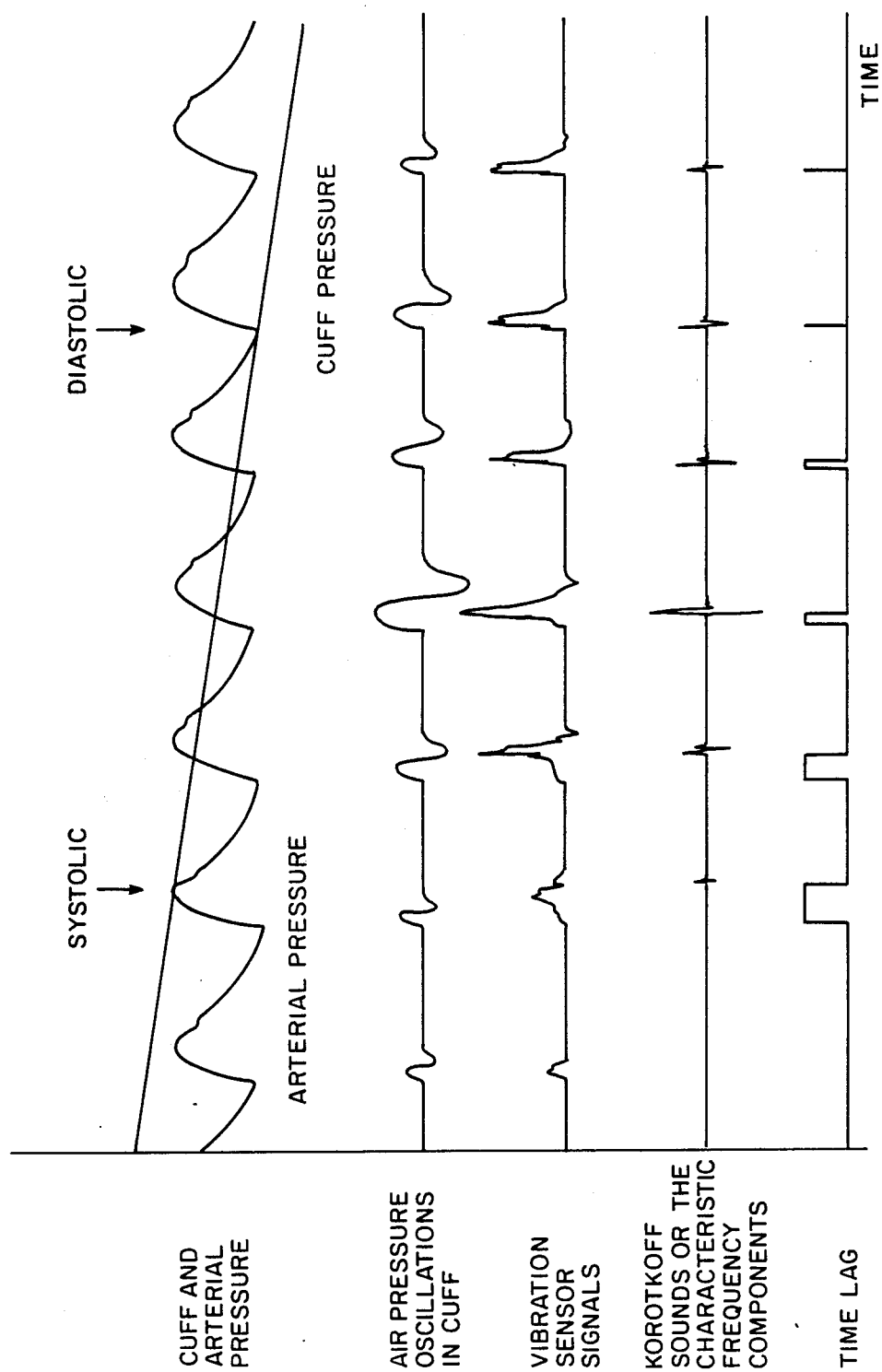
FIG. 1 is a wave diagram of signals generated by a cuff bladder.

When cuff pressure falls below systolic, Korotkoff sounds appear and the sensor signal contains both the low frequency and the characteristic frequency components. Blood flow, the Korotkoff sound and the characteristic frequency component are all initiated at the moment when each arterial pressure pulse rises to the same level as the descending cuff pressure; see FIG. 1. It is therefore apparent that the generation of Korotkoff sound lags behind the arterial pressure wave. The time lag between the rise of the arterial pressure pulse, i.e., the arrival of the ascending wave, and the generation of Korotkoff sound is at its maximum near the systolic pressure, decreases as the cuff pressure is lowered, and diminishes as the cuff pressure approaches the true diastolic pressure. Below diastolic pressure, the time lag appears to be zero or become undefined when the Korotkoff sound or the characteristic frequency component disappear altogether. In other words, at or below diastolic pressure, any Korotkoff sounds (or the characteristic frequency component), if they exist, will be in phase with the arterial pressure wave and therefore in phase with the air pressure oscillations within the cuff.

Therefore, the cuff pressure at the point when the time lag reaches zero can be identified as the diastolic pressure. An illustration of the phase discrimination method is presented in FIG. 2.

It has been reported that in 37% of blood pressure measurements, muffling coincides with the last sound or is completely absent. In such case, the Korotkoff sound may sometimes disappear before the time lag actually reaches zero, therefore, the cuff pressure corresponding to the minimum time lag (i.e., the last sound) is taken as the closest approximation to the actual diastolic pressure.

In the remaining 63% of blood pressure measurements, both Phase IV and Phase V exist. It is generally believed that the real diastolic pressure index falls between Phase IV and V. Below diastolic pressure, the artery is not occluded but is deformed by the cuff pressure, resulting in a non-circular cross-section. If streamline flow is restored, no sound can be heard (in 37% of all cases). If in such subjects a streamline flow is not restored after diastolic pressure, Korotkoff sounds may persist. In other words, a deformed artery below diastolic pressure results in arterial wall movement, disturbed flow, turbulence, vortices and, therefore, sound. It is in this group of people the present method is most valuable It is known that "Korotkoff vibrations" can be detected in shock patients in whom the Korotkoff sounds are unobservable. The term "Korotkoff vibration" is used to describe board spectrum arterial vibrations detected by a sensor using the techniques of sphygmomanometry. From this "Korotkoff vibration", which may be audible or inaudible, one can extract the characteristic frequency component and therefore, apply our phase discrimination method.

EXAMPLE

In this example the arterial pressure (first signal) in mm Hg was established from a standard curve; the next suceeding Korotkoff sound was detected in mm Hg using an electret microphone and the time lag was determined using a monostable multivibrator circuit.

Figure 3:
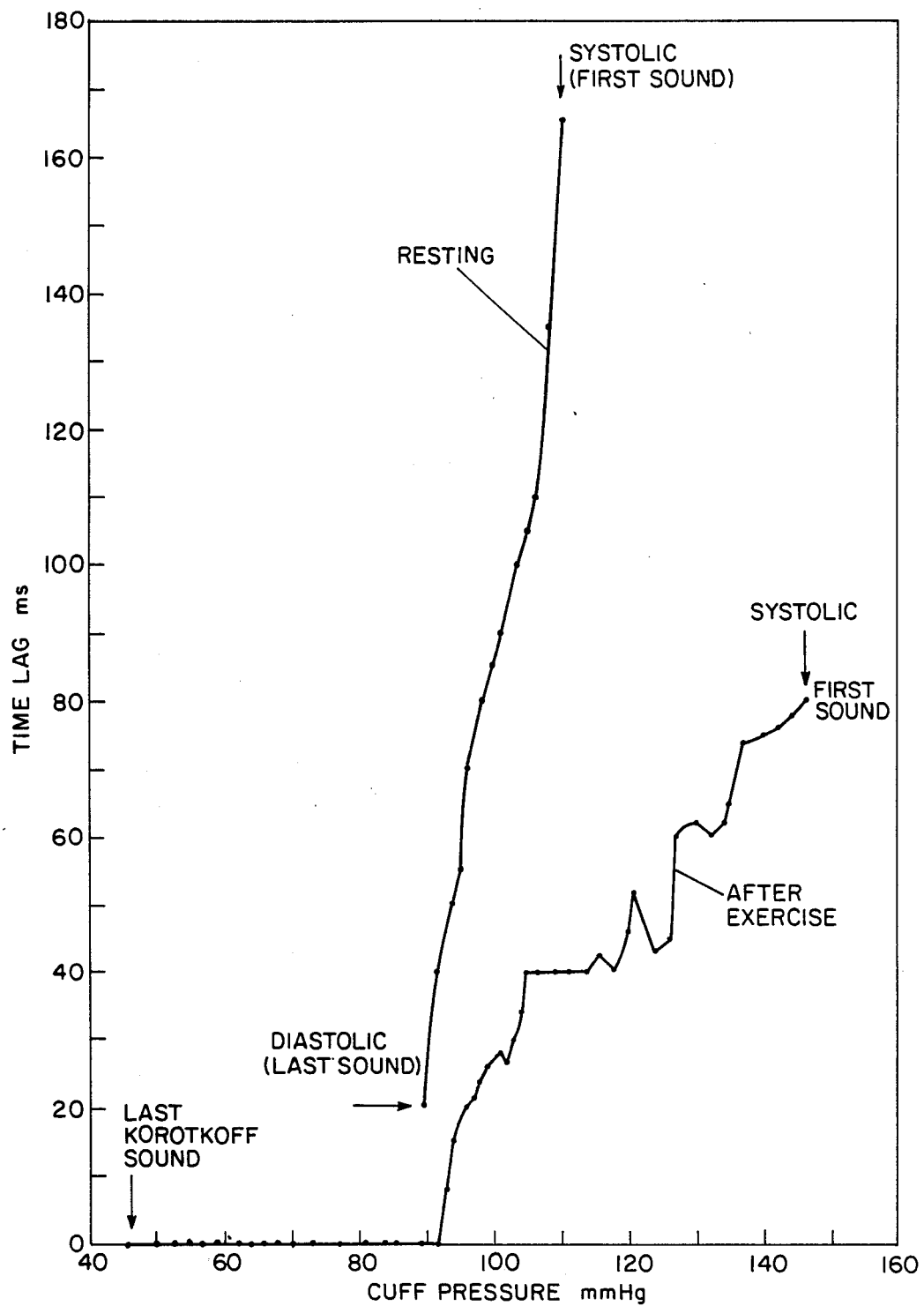
FIG. 3 is a graph of test results generated using the inventive method.

The time lag has been measured in a normal subject, FIG. 3. During resting, the systolic/diastolic pressure was 110/90 mmHg. Each point on the curve represents the data point of a cardiac cycle during which a Korotkoff sound was heard. For this subject, the Phase IV and V appear to coincide. The time lag was 165 ms at the first sound (systolic pressure) and decreased to 20 ms at the last sound (diastolic pressure).

In order to artificially create a Phase V, the same subject was instructed to run in place for approximately 2 minutes. Measurements were resumed immediately after exercise. The first sound appeared at 146 mmHg with time lag of 80 ms. The time lag reached zero at 92 mmHg which was diastolic pressure. The last Korotkoff wound was heard at a cuff pressure of 46 mmHg.

My method allows a unique determination of diastolic pressure to be made without the dilemma, of choosing Phase IV, Phase V or other haphazard criteria. The phase discrimination method depends on "upstream" conditons only. It is least affected by artificially created condition such as venous congestion which may develop downstream from the occluding cuff (i.e., any conditon which exists distal to the occlusion point will not affect diastolic pressure determination). The unit will still function with a tourniquet applied on the distal edge of the cuff. It is ideally suited for indirect diastolic pressure determination in infants, young children, patients with aortic regurgitation, animals, normal subjects after exercise and other cases when Phase IV/-Phase V determination is either inaccurate, difficult, subjective or hearing-acuity dependent.

Because the proposed method makes differential time measurement of two events and it is independent of the signal intensity per se, it provides more accurate and reliable measurements when the patient in shock is clad in chemical warfare protective garments through which the sensor signal may be significantly attenuated.

Lastly, the present method is not limited to normal subjects in whom Korotkoff sounds can be heard. For patients in clinical shock, as long as the sensor is capable of detecting sub-audible vibrations, the characteristic frequency component of the Korotkoff signal would still be present even though the conventional "Korotkoff sound" may not exist.

Another aspect of the invention relates to use of the method in motion artifact rejection. Motion artifact rejection is an important aspect in the design of blood pressure monitors even for those intended to be used in a hospital setting.

Figure 2:
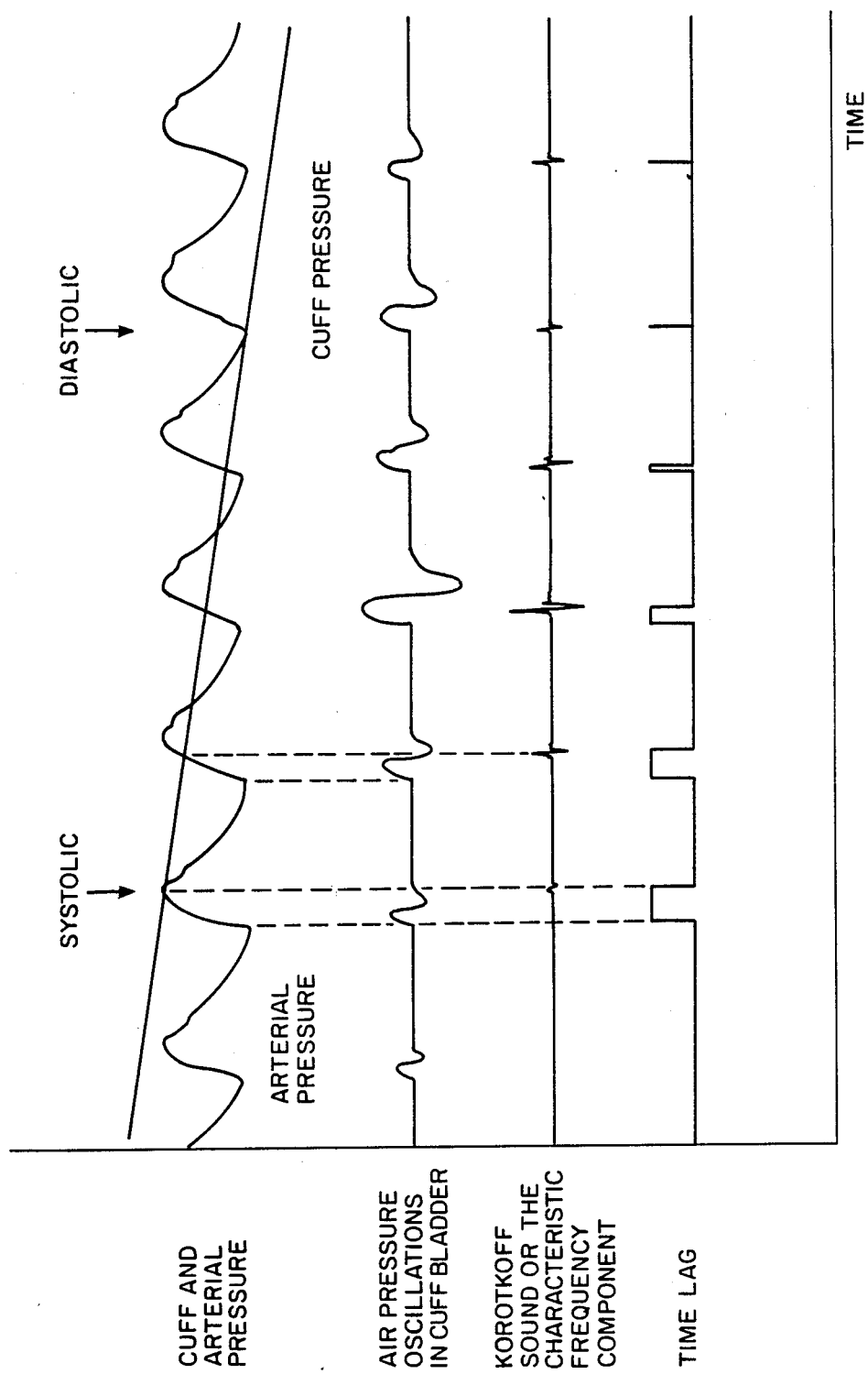
FIG. 2 is a graphical respresentation of the phase discrimination technique.

Referring to FIG. 2, the true Korotkoff signals always lag behind (the ascending branch of) the air pressure oscillations. On the other hand, motion artifacts invariably create simultaneous disturbances in both the electret transducer channel and the air pressure channel. Therefore, any signal (from the electret transducer) which is in phase with the air pressure oscillation will be regarded as either noise or the unwanted signal below true diastolic pressure, and will, therefore, be rejected. Accordingly, our invention is also useful in overcoming motion artifacts.

Having described our invention, what we now claim is:

1. A method of measuring diastolic pressure wherein a cuff bladder is used which includes:
    sensing the arrival of an arterial pressure pulse said sensing independent of the time segment between the R-wave and said arterial pressure pulse;
    sensing the initiation of a subsequent Korotkoff sound;
    measuring the time lag between the arrival of the pressure pulse and the initiation of the Korotkoff sound; and
    providing an output corresponding to the diastolic pressure when there is no measurable time lag between the arrival of the pressure pulse and the Korotkoff sound.

2. The method of claim 1 which includes determining the arrival of the arterial pressure pulse from oscillometric signals which signals are generated by the striking action of the arterial pressure wave train against the proximal edge of a cuff bladder.

3. The method of claim 1 wherein the sensing of the Korotkoff sound includes detecting a characteristic frequency component which component corresponds to arterial wall motion and turbulent blood.

4. The method of claim 1 wherein a sensor is disposed in the cuff bladder which sensor generates a low frequency component which component corresponds to the arrival of the arterial pressure pulse.

5. A method of providing a signal substantially free of motion artifacts which includes:
    sensing the arrival of an arterial pressure pulse;
    sensing the initiation of a subsequent Korotkoff sound;
    measuring the time lag between the arrival of the pressure pulse and the initiation of the Korotkoff sound; and,
    outputting a signal substantially free of motion artifacts.

6. The method of claim 1 wherein the sensing of the Korotkoff sound includes:
    detecting a wave derived from arterial wall motion.

* * * * *